United States Patent
Choi et al.

(10) Patent No.: US 9,650,663 B2
(45) Date of Patent: May 16, 2017

(54) SENSOR FOR DETECTING STEM CELL DIFFERENTIATION BASED ON ELECTROCHEMICAL METHODS

(71) Applicant: Industry-University Cooperation Foundation Sogang University, Seoul (KR)

(72) Inventors: Jeong-Woo Choi, Seoul (KR); Cheol-Heon Yea, Seoul (KR)

(73) Assignee: Industry-University Cooperation Foundation Sogang University, Seoul (KR)

(*) Notice: Subject to any disclaimer, the term of this patent is extended or adjusted under 35 U.S.C. 154(b) by 0 days.

(21) Appl. No.: 14/092,046

(22) Filed: Nov. 27, 2013

(65) Prior Publication Data

US 2014/0158554 A1 Jun. 12, 2014

Related U.S. Application Data (63) Continuation of application No. 12/579,084, filed on Oct. 14, 2009, now abandoned.

(30) Foreign Application Priority Data

Mar. 27, 2009 (KR) .................. 10-2009-0026353

(51) Int. Cl.
- *C12Q 1/42* (2006.01)
- *C12Q 1/00* (2006.01)
- *C12N 5/0735* (2010.01)

(52) U.S. Cl.
CPC .............. *C12Q 1/42* (2013.01); *C12Q 1/005* (2013.01); *C12N 5/0606* (2013.01)

(58) Field of Classification Search
CPC ......... C12Q 1/42; C12Q 1/005; C12N 5/0606
USPC ............ 205/777.5; 424/93.1–93.73; 435/325
See application file for complete search history.

(56) References Cited

U.S. PATENT DOCUMENTS

| | | | |
|---|---|---|---|
| 6,800,480 B1 * | 10/2004 | Bodnar et al. | 435/325 |
| 2005/0079484 A1 * | 4/2005 | Heineman et al. | 435/5 |

OTHER PUBLICATIONS

Berger et al., "Secreted placental alkaline phosphatase: a powerful new quantitative indicator of gene expression in eukaryotic cells," Gene, Jun. 15, 1988; vol. 66(1); pp. 1-10.

(Continued)

*Primary Examiner* — Matthew Martin
*Assistant Examiner* — Kourtney S Carlson
(74) *Attorney, Agent, or Firm* — Locke Lord LLP; Gabriel J. McCool (57) ABSTRACT

This invention relates to a sensor for detecting a stem cell differentiation, including (a) an electrode; and (b) a substrate of an alkaline phosphatase. The phosphorylation or dephosphorylation of the substrate for an alkaline phosphatase as a stem cell undifferentiation marker which dephosphorylates its substrate may be measured using an electrical signal in the present sensor. Therefore, the sensor of the present invention enables to electrically detect a stem cell status in a high-throughput manner and to determine the stem cell differentiation.

1 Claim, 9 Drawing Sheets

(56) References Cited

OTHER PUBLICATIONS

Kelso et al., "Electrochemical Detection of Secreted Alkaline Phosphatase: Implications to Cell Based Assays," Electroanalysis; 2000; vol. 12, No. 7; pp. 490-494.
MacGregor et al., "Tissue non-specific alkaline phosphatase is expressed in both embryonic and extraembryonic lineages during mouse embryogenesis but is not required for migration of primordial germ cells," Development, 1995, vol. 121; pp. 1487-1496.

\* cited by examiner

SENSOR FOR DETECTING STEM CELL DIFFERENTIATION BASED ON ELECTROCHEMICAL METHODS

CROSS-REFERENCE TO RELATED APPLICATION

This is a continuation application of Application No. 12/579,084 filed on Oct. 14, 2009, which claims under 35 U.S.C. §119(a) the benefit of Korean Application No. 10-2009-0026353 filed Mar. 27, 2009, which applications are incorporated herein by reference.

BACKGROUND

1. Technical Field

The present invention relates to a sensor for detecting a stem cell differentiation, including: (a) an electrode; and (b) a substrate for an alkaline phosphatase.

2. Background Art

Cell chip technology is a promising tool for utilization in cell based assays. There are two kinds of cell detection systems for these chips. These systems are based on optical detection and electrical (electrochemical) detection respectively. Optical systems allow one to observe visual changes of the cells and have high sensitivity and selectivity. Optical systems are limited by size of the instrument and the process of transforming the optical signal into an electrical signal [1-2].

While electrical cell detecting systems are relatively less developed than optical systems, they have the ability to be miniaturized and the signals are easily analyzed. There have been some attempts to analyze living cells as electrochemically dynamic systems by detecting electron generation and electron transfer at the interface [3].

Living cells have been studied by many electrochemical situations such as electron transfer at electro active centers in cells, open circuit potential at the cell/sensor interface, electric cell-substrate impedance sensing (ECIS), scanning electrochemical microscopy (SECM) to obtain images of the respiratory activity of collagen-embedded living cells, electrochemical impedance spectroscopy (EIS), and activation of an oxygen electrode [4-11].

However, there has been no attempt to detect the differentiation of MES cells using electrical or electrochemical systems.

The above information disclosed in this Background section is only for enhancement of understanding of the background of the invention and therefore it may contain information that does not form the prior art that is already known in this country to a person of ordinary skill in the art.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have intensive studies to develop a novel sensor and method for detecting a stem cell differentiation based on electrochemical methods. As results, we have discovered that the phosphorylation or dephosphorylation of the substrate for alkaline phosphatase as a stem cell undifferentiation marker which dephosphorylates its substrate could be measured using an electrical signal to determine a stem cell differentiation in an electrochemical manner.

Accordingly, it is an object of the invention to provide a sensor for detecting a stem cell differentiation.

It is another object of this invention to provide a method for determining a stem cell differentiation.

Other objects and advantages of the present invention will become apparent from the detailed description to follow taken in conjugation with the appended claims and drawings.

DETAILED DESCRIPTION

In one aspect of this invention, there is provided a sensor for detecting a stem cell differentiation, including: (a) an electrode; and (b) a substrate for an alkaline phosphatase.

The present inventors have intensive studies to develop a novel sensor and method for detecting a stem cell differentiation based on electrochemical methods. As results, we have discovered that the phosphorylation or dephosphorylation of the substrate for alkaline phosphatase as a stem cell undifferentiation marker which dephosphorylates its substrate could be measured using an electrical signal to determine a stem cell differentiation in an electrochemical manner.

The sensor for detecting the stem cell differentiation of the present invention is constituted of a conventional three-electrode system known to those ordinarily skilled in the art, which includes a working electrode, a counter electrode and a reference electrode.

According to a preferable embodiment, the electrode involved in the sensor of the present invention is selected from the group consisting of a gold, copper, glass carbon, platinum and Ag/AgCl electrode. More preferably, the electrode includes a gold, copper or glass electrode as the working electrode, a platinum electrode as the counter electrode, and a Ag/AgCl electrode as the reference electrode, and most preferably a gold electrode as the working electrode, a platinum electrode as the counter electrode, and a Ag/AgCl electrode as the reference electrode.

The alkaline phosphatase used in the present invention refers to a marker representing an undifferentiation status of stem cells.

The substrate for alkaline phosphatase contained in the sensor of the present invention may include various compounds containing a phosphate group known to those ordinarily skilled in the art, preferably 1-naphthyl phosphate, calcium phosphate, phenyl phosphate, 2-aminophenyl phosphate, 4-aminophenyl phosphate, p-aminophenyl phosphate, 3-indoxyl phosphate, 5-bromo-4-chloro-3-indoxyl phosphate, 4-methylumbelliferyl phosphate, 6-chloro-3-indoxyl phosphate or hydroquinone diphosphate, more preferably 1-naphthyl phosphate, phenyl phosphate, 2-aminophenyl phosphate, 4-aminophenyl phosphate or 3-indoxyl phosphate, and most preferably 1-naphthyl phosphate.

Figure 1:
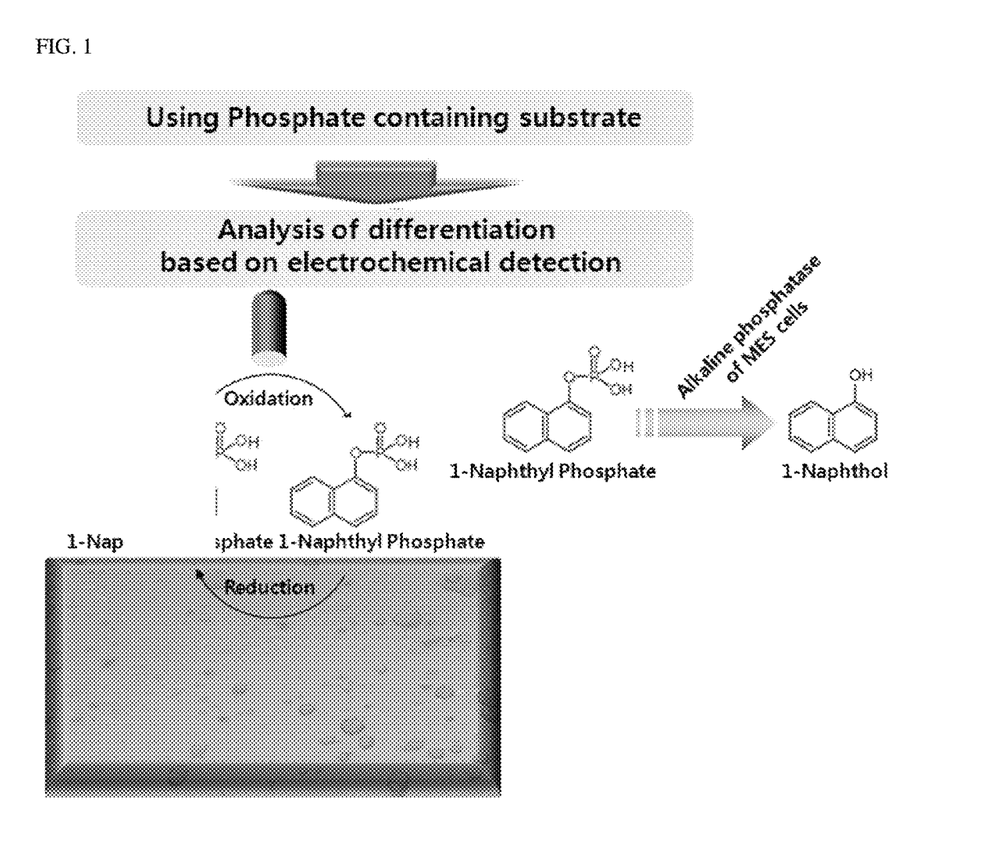
FIG. 1 schematically represents the electrochemical detection system in which 1-naphthyl phosphate (NP) as a substrate of an alkaline phosphatase (AP) involved in the sensor of the present invention is changed into 1-naphtol by the alkaline phosphatase of a mouse embryonic stem cell undifferentiated.
Figure 2A:
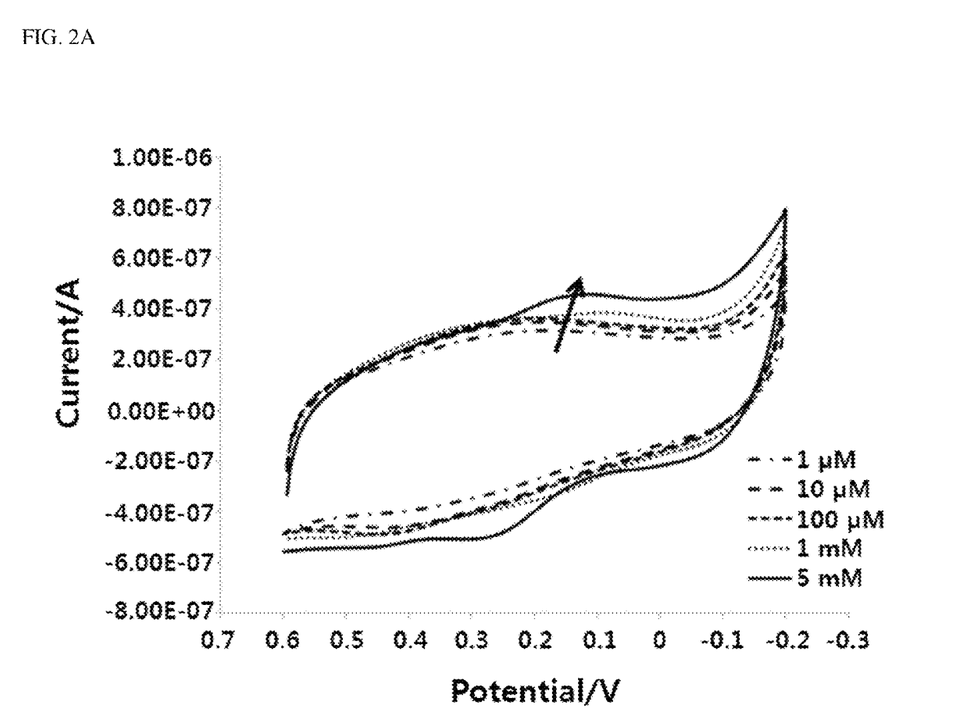
FIG. 2A represents a cyclic voltammogram of 1-NP used as a substrate in the sensor of the present invention and FIG. 2B represents a linear plot of reduction current peak as increasing concentration of 1-NP.
Figure 2B:
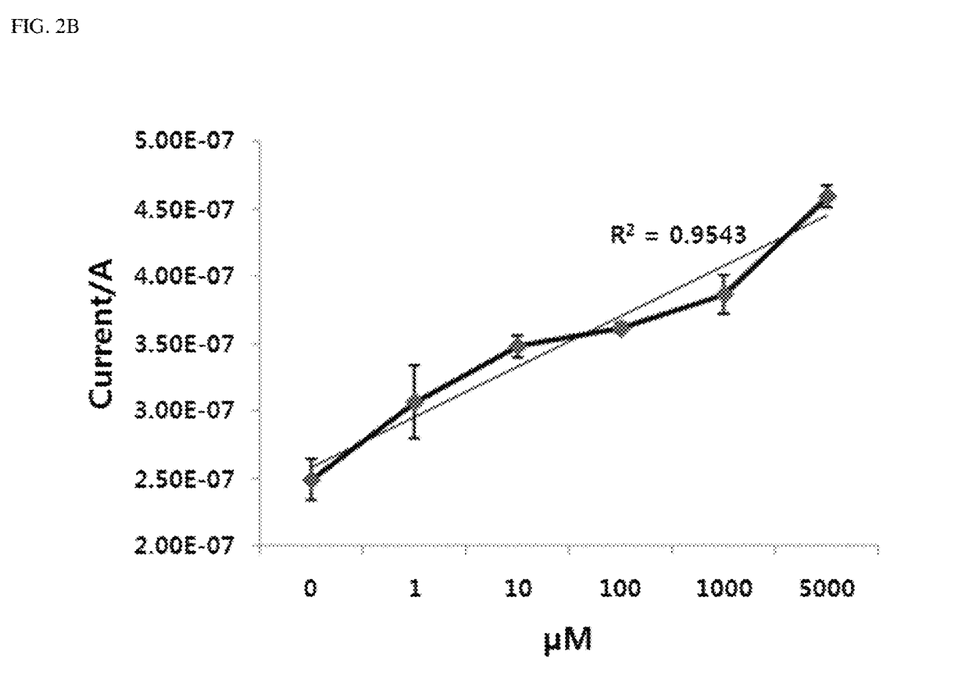

In particular, 1-naphthyl phosphate as a substrate for alkaline phosphatase is a compound in which the phosphate group is linked to two benzene rings (FIG. 1), and is dephosphorylated by alkaline phosphatase present in undifferentiated stem cells so as to be changed into 1-naphtol. It is demonstrated that the electrochemical characteristics of the modified substrate have quite different to those of the pre-modified substrate (FIG. 2).

According to another preferable embodiment, the stem cell used in the sensor of the present invention is an embryonic stem cell or a germ stem cell, and more preferably an embryonic stem cell.

According to still another preferable embodiment, the stem cell used in the sensor of the present invention is a human or mouse-derived stem cell, and more preferably a mouse-derived stem cell.

According to further still another preferable embodiment, the stem cell used in the sensor of the present invention includes an alkaline phosphatase where the stem cell is an undifferentiated stem cell; and the stem cell includes no alkaline phosphatase where the stem cell is a differentiated stem cell.

According to another preferable embodiment, the sensor of the present invention measures the phosphorylation or dephosphorylation of alkaline phosphatase substrate using an electrical signal to determine the differentiation of the stem cell.

According to still another preferable embodiment, the substrate dephosphorylated by alkaline phosphatase in the present invention includes 1-naphtol, calcium ion, phenol, 2-aminophenol, 4-aminophenol, p-aminophenol, 3-indoxol, 5-bromo-4-chloro-3-indoxol, 4-methylumbelliferol, 6-chloro-3-indoxol or hydroquinone, more preferably 1-naphtol, phenol, 2-aminophenol, 4-aminophenol or 3-indoxol, and most preferably 1-naphtol.

In another aspect of this invention, there is provided a method for determining a stem cell differentiation, comprising the steps of: (a) preparing the sensor for detecting the stem cell differentiation; (b) contacting cells of interest to the sensor; and (c) measuring the phosphorylation or dephosphorylation of a substrate for alkaline phosphatase on the cells through an electrical signal.

To examine whether the stem cells are differentiated or not, the method according to the step of this invention is minutely explained as follows:

(a) The step preparing the sensor for detecting the stem cell differentiation.

The sensor for detecting a stem cell differentiation containing an electrode; and a substrate for an alkaline phosphatase is prepared.

Since the electrode of the sensor and the substrate for the alkaline phosphatase are described above, the common descriptions between them are omitted in order to avoid undue redundancy leading to the complexity of this specification.

(b) The step contacting cells of interest to the sensor.

And then, the stem cells of interest are contacted to the sensor for verifying a differentiation status.

(c) The step measuring the phosphorylation or dephosphorylation of the substrate for alkaline phosphatase on the cells through an electrical signal.

The substrate is dephosphorylated by alkaline phosphatase in undifferentiated stem cells, and the substrate dephosphorylated may be measured using a cyclic voltammetry because the modified substrate has quite different electrochemical properties compared to the pre-modified substrate.

Data for undifferentiated stem cells may be quantitated by tracing the electrochemical signal of the alkaline phosphatase substrate using its electrochemical characteristics, and the signal of the alkaline phosphatase substrate changed according to differentiation may be detected using an electrochemical method to determine the differentiation of the stem cell.

Likewise, the electrochemical signal of the alkaline phosphatase substrate in the undifferentiated stem cells is quantitated according to the amounts of stem cells, and the electrochemical signal of the alkaline phosphatase substrate in the differentiated stem cells is also quantitated according to the amounts of stem cells. And then, these results are compared to determine the extent of the stem cell differentiation.

Figure 4:
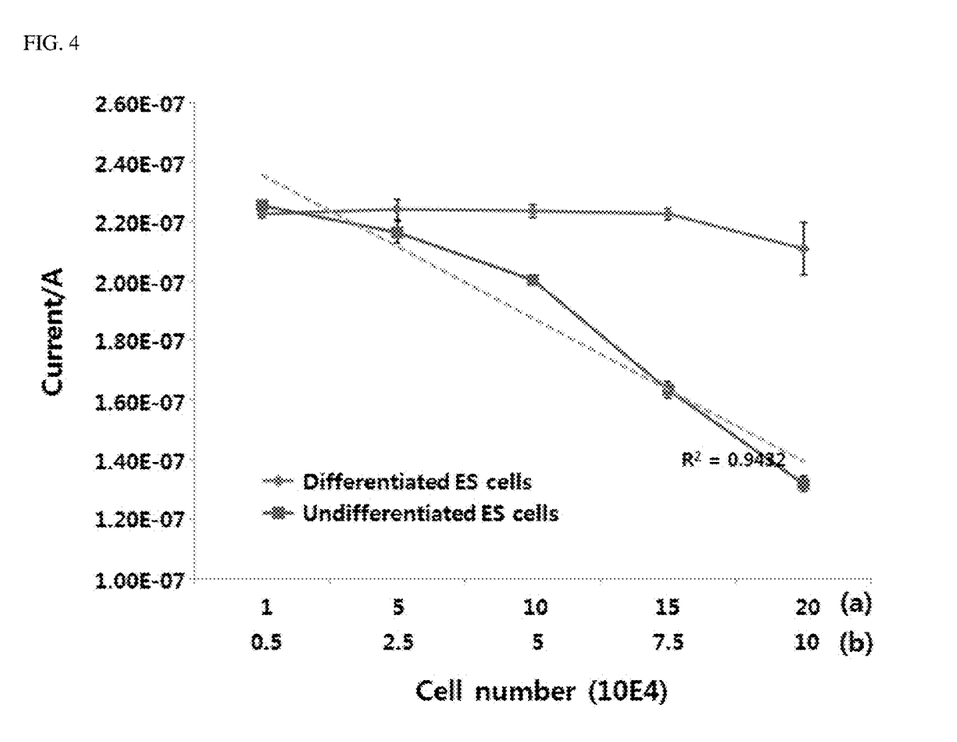
FIG. 4 is a linear plot of reduction current peak as increasing concentration of (a) differentiated MES cells (ES cells) and (b) undifferentiated MES cells (ES cells). The scan rate was 100 mV/s. The temperature was 37±0.5° C. and the $CO_2$ was 5%. Data are presented as the mean±standard deviation of three different experiments.

In a view of identifying the differentiation of mouse embryonic stem (MES) cells as a preferable embodiment, differentiated MES cells show an independent relationship between electrical signal and increasing cell number, while undifferentiated MES cells represent a linear correlation between electrical signal and increasing cell number. $R^2$ value representing the linearity of undifferentiated MES cells is significantly calculated as 0.9432, indicating that the cell status could be identified using this electrochemical method and the detection limit is 50,000 undifferentiated MES cells (FIG. 4).

As described above in detail, the present invention provides a sensor for detecting a stem cell differentiation, including (a) an electrode; and (b) a substrate for an alkaline phosphatase. The phosphorylation or dephosphorylation of the substrate for an alkaline phosphatase as a stem cell undifferentiation marker which dephosphorylates its substrate may be measured using an electrical signal in the present sensor. Therefore, the sensor of the present invention enables to electrically detect a stem cell status in a high-throughput manner and to determine the stem cell differentiation.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Materials and Methods

2.1 Materials

1-Naphthyl phosphate and phosphate buffered saline (PBS) (pH 7.4, 10 mM) solution was purchased from Sigma-Aldrich. All other chemicals that are used in this study were obtained commercially as reagent grade.

2.2 Undifferentiated MES Cell Culture and Embryonic Body formation

J1 cells, mouse embryonic stem (ES) cells, were cultured in Dulbecco's modified Eagle's medium (DMEM) supplemented with 15% FBS, 1 mM sodium pyruvate, $10^{-4}$M 2-mercaptoethanol, 1×nonessential amino acids, and 1,000 U of leukemia inhibitory factor (LIF) per ml at 37° C. and 5% $CO_2$. EB formation was performed with J1 ES cells as previously described [13]. ES cells ($2 \times 10^6$ cells) were seeded onto the bacterial-grade Petri dishes in DMEM containing 10% FBS without LIF. After 2 days of suspension culture, EBs were collected and trypsinized. A total of $1.37 \times 10^6$ cells were replated on 0.2% gelatin-coated 6-well plates containing the same medium. The number of cells was counted after 3 days.

2.3 Fabrication of Electrochemical Cell

The culture chamber is a regular square chamber and each side is 2 mm long. We used 1the working gold electrode (CHI101), the Ag/AgCl reference electrode (CHI111), and the platinum counter electrode (CHI115). The J1 cells were transferred into the chamber at a known cell density by infusion with fresh culture medium. The number of cells was determined by a trypan blue dye method using a hemacytometer.

2.4 Electrochemical Sensing of MES Cells

The cyclic voltammetry experiments were performed using a CHI660A machine controlled by a general electrochemical system software. A three-electrode system was designed which was comprised of the gold as the working electrode, a platinum wire as the counter electrode, and an Ag/AgCl cell as the reference electrode. Measurements were carried out to study the electrical properties of MES cells as well as detect the differentiation of the mouse embryonic stem cells by the interaction between 1-NP and differentiation marker alkaline phosphatase. PBS (10 mM, pH 7.4) was used as an electrolyte at a scan rate of 0.1 V/s. Before the experiment occurs, the culture media was removed and the 1-NP containing PBS was injected into the chamber. The experiment was started 15 min after buffer changing, and the measurement conditions were maintained at 37° C., 5% $CO_2$.

2.5 Alkaline Phosphatase Staining Immunoassay

Alkaline Phosphatase (AP) staining immunoassay kit was purchased from Sigma-Aldrich. First, the cells were fixed using a citrate-acetone-formaldehyde fixative solution. After fixation, an alkaline-dye mixture which is composed of sodium nitrate, FRV-alkaline solution, and naphthol AS-BI alkaline solution was added to the cells in a dark room and allowed to stain for 15 min. Finally, the cells were counterstained using hematoxylin solution.

3. Results

3.1 Signal Detecting of 1-Naphtyhyl Phosphate

We quantified the 1-NP signal as follows. The concentration of 1-NP was ranged from 1 μm to 5 mM in an electrolyte buffer of 10 mM PBS (FIGS. 2A-2B). FIG. 2A describes the electrochemical property of the 1-NP. The peak was observed around 0.1 V and the potential slowly changed to negative voltage as the concentration of 1-NP decreased. FIG. 2B shows the direct, linear, relationship between 1-NP peak current and concentration of 1-NP. Linear regression analysis was performed which proved the reliability of the electrochemical quantifying method using cyclic voltammetry ($R^2=0.9543$). These results indicate that 1-NP can be quantified by this cyclic voltammetry assay.

3.2 Electrochemical Response of Undifferentiated MES Cells

Figure 3A:
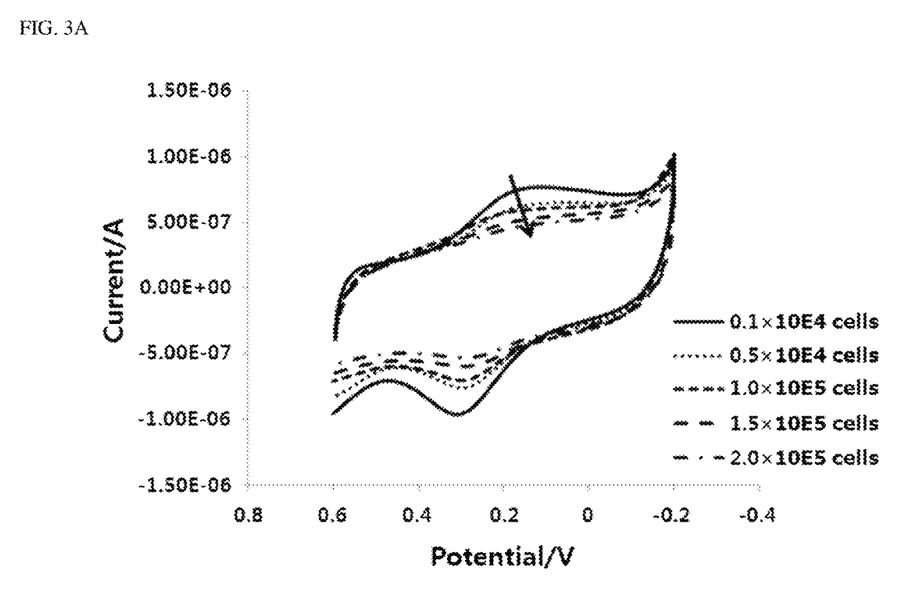
FIG. 3A represents a cyclic voltammogram of mouse embryonic stem cells according to addition of 1-NP and FIG. 3B represents a linear plot of reduction current peak as increasing concentration of MES cells. Data are presented as the mean ±standard deviation of three different experiments. Arrow indicates increasing cell number.
Figure 3B:
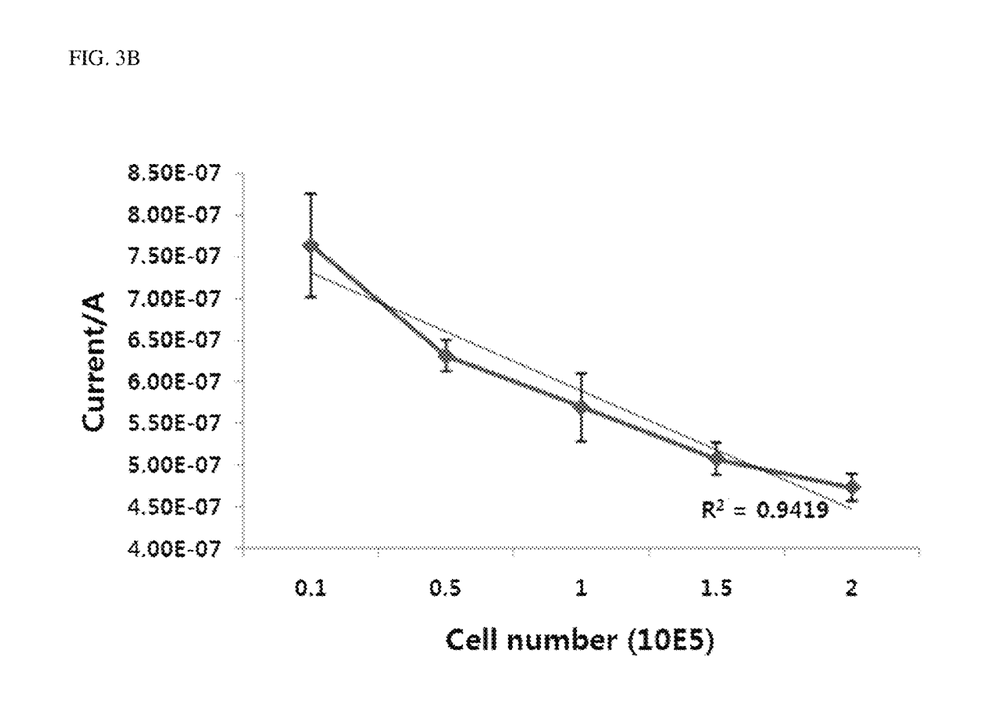

By incorporating 1-NP into the substrate of the MES cells, alkaline phosphatase (an embryonic stem cell marker) can be tracked by its dephosphorylating action on 1-NP. When the dissolved 1-NP changes to 1-Naphthol there is a corresponding change in electrical signal as 1-Napthol cannot be seen by the boundary conditions set up to detect 1-NP. The detection was performed in 15 minutes after the 1-NP was injected. FIG. 3A shows the electrochemical property of MES cells after addition of 1-NP. The entire potential was slightly changed to positive direction, but the reduction peak current was decreased with an increasing concentration of MES cells. The reason for this potential change could include the media, because media has a lot of different materials. The linear plot is showed in FIG. 3B and the linear regression analysis is represented by $R^2$ value, 0.9419. These results indicate good correlation between cell number and CV reduction current peak which is estimated to 1-NP.

3.3 Detecting Differentiation of MES Cells

In order to detect the differentiation of MES cells, we compared electrochemical signals from undifferentiated MES cells and differentiated MES cells. Each group of cells was seeded into a culture chamber to a specific cell number. Because the undifferentiated MES cells have better adhesion and growth than differentiated MES cells, we seeded two times more differentiated cells than the undifferentiated MES cells.

FIG. 4 shows the relationship between undifferentiated MES cells and differentiated MES cells. Differentiated MES cells showed an independent relationship between electrical signal and increasing cell number, while undifferentiated MES cells showed a linear relationship between signal and cell number. The linearity of undifferentiated MES cells is represented by a high $R^2$ value of 0.9432. The P-value for reliability between undifferentiated MES cells and differentiated MES cells is 0.095, 0.001, 0.006 and 0.002 respectively for each point starting from the second data point of the cell number. Other than the lowest two cell numbers, all other points were significantly different at a 5% confidence level. That means the third point of cell number is the detection limit to identify the differentiation of MES cells. These results indicate that we could identify the cell status using this electrochemical method and the detection limit is 50,000 undifferentiated MES cells.

3.4 1-Naphthyl Phosphate Effect to Mouse MES Cells

Figure 5A:
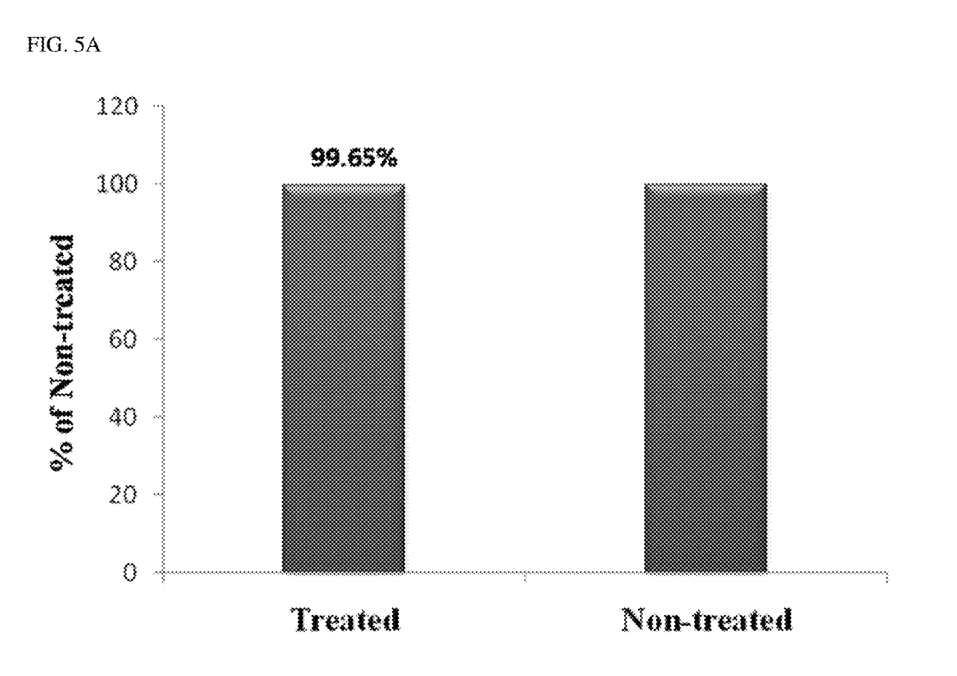
FIG. 5A represents a viability test according to 1 mM 1-NP treatment. Data are presented as the mean of three different experiments.
Figure 5B:
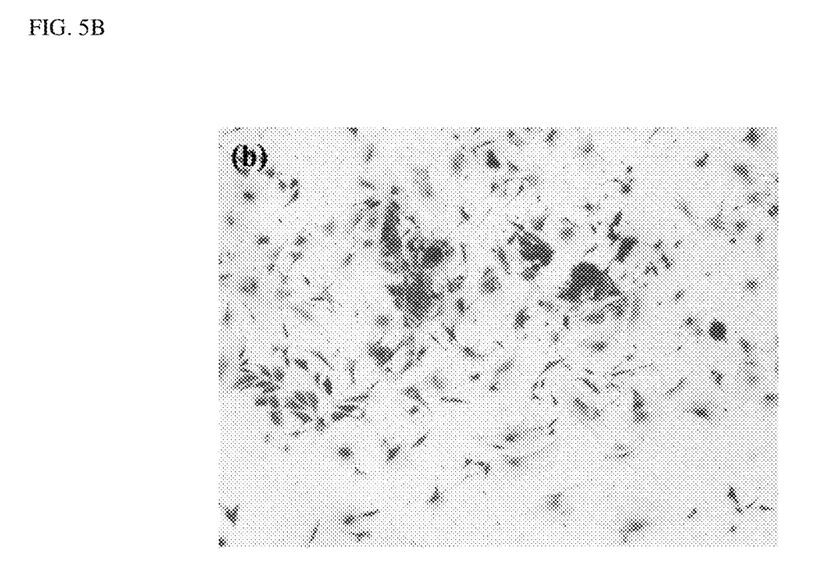
FIGS. 5B and 5C represent AP staining assay of (FIG. 5B) undifferentiated MES cells and (FIG. 5C) MES cells treated with 1-NP.
Figure 5C:
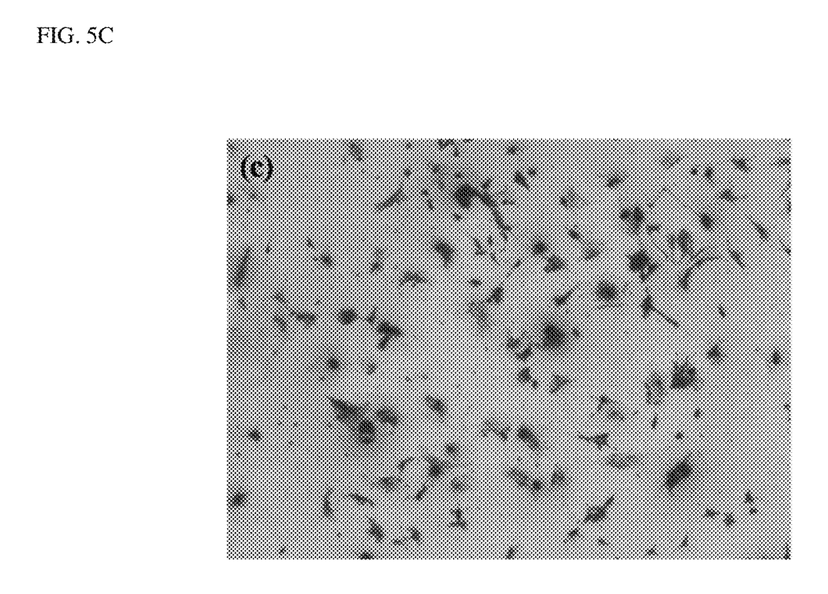

To ensure that the presence of 1-NP is not affecting our tests by altering MES cell viability or differentiation, an Alkaline Phosphatase (AP) staining assay was performed. FIG. 5A shows the result of the viability test after treating the cells with 1 mM 1-NP. The cell viability was 99.65% as compared with control. FIGS. 5B and 5C show the results of AP staining before NP treated stem cells and after NP treated stem cells. Each figure shows well stained stem cells, which means that 1-NP does not affect the differentiation of stem cells.

4. Discussion

In this paper, we propose a cell based sensor that could detect differentiation of MES cells based on electrochemical tools. Electrochemical cell based sensors have been investigated before, but most of them are used for detecting cell viability. These kinds of cell based sensor have been applied to drug screening of cancer cells or to environmental toxicant effect to cells [12].

Electrochemical cell based sensors can be divided into two groups based on measuring techniques. One technique is based on measuring impedance [14-16]. Cells are generally insulative. If cells cover a large area of the electrode, there is a relatively high level of impedance. In order for this technique to work the cells must be able to attach to the electrode surface. This limits this technique's usefulness to cells which are the type to be adherent. This technique is based on the assumption that the surface attached cells are alive and detached cells are dead.

Another type of electrochemical cell based sensor utilizes an amperometric technique [6]. Amperometric technique involves detecting electrical current with a fixed potential. Sometimes CV technique is introduced as a means to determine the potential for an amperometric technique. The amperometric technique measures the amount of oxygen and the amount of dopamine around cells to determine cell viability. Recently, the signal of HeLa cell was quantified by CV and Potential Stripping Analysis (PSA) techniques [12]. However, to date there has been no attempt to measure the differentiation of stem cells using electrical or electrochemical tools.

In summary, we report the successful demonstration of identifying and quantifying ES cell differentiation utilizing a novel technique base on 1-NP measured via an electrochemical method. We have shown that measuring the 1-NP is a feasible means to determine ES cell differentiation, and the presence of this indicator did not affect the viability and differentiation of these cells. For this experiment, we tested 1-NP as a substrate for detecting the differentiation of MES cells. We have successfully quantified the 1-NP by an electrochemical method, and this technique was applied to MES cells to detect the differentiation status of the cells. The peak current of 1-NP increases only with undifferentiated MES cell number indicating that 1-NP only reacts with undifferentiated MES cells. Finally, we compared the signal of differentiated MES cells and undifferentiated MES cells, and we determined the detection limit of undifferentiated MES cell number to be≥50,000. The proposed electrochemical measurement system can be applied to electrical stem cell chip for diagnosis, drug detection and on-site monitoring.

REFERENCES

[1] Michalet X, Pinaud F F, Bentolila L A et al. Quantum dots for live cells, in vivo imaging, and diagnostics. *Science* 2005; 307: 538-544.
[2] Zhu L, Wu W, Zhu M Q et al. Reversibly photoswitchable dual-color fluorescent nanoparticles as new tools for live-cell imaging. *J Am Chem Soc* 2007; 129; 3524-3526.
[3] Matsunaga T, Namba Y. Detection of microbilal cells by cyclic voltammetry. *Anal Chem* 1984; 56: 798-801.
[4] Bard A J, Li X, Zhan W. Chemically imaging living cells by scanning electrochemical microscopy. *Biosens Bioelectron* 2006; 22: 461-472.
[5] Lu H, Gratzi M. Monitoring drug efflux from sensitivity and multidrug-resistant single cancer cells with microvoltammetry. *Anal Chem* 1999; 71: 2821-2830.
[6] Cui H F, Ye J S, Chen Y et al. Microelectrode array biochip: Tool for in vitro drug screening based on the detection of a drug effect on dopamine release from PC12 cells. *Anal Chem* 2006; 78: 6347-6355.
[7] Fasching R J, Bai S J, Fabian T, Prinz F B Nanoscale electrochemical probes for single cell analysis. *Microelectron Eng* 2006; 83: 1638-1641.
[8] Kaya T, Torisawa Y, Oyamatsu D et al. Monitoring the cellular activity of a cultured single cell by scanning electrochemical microscopy (SECM). A comparison with fluorescence viability monitoring. *Biosens Bioelectron* 2003; 18: 1379-1383.
[9] Kasai S, Shiku H, Torisawa Y et al. Cytokine assay on a cellular chip by combining collagen gel embedded culture with scanning electrochemical microscopy. *Anal Chim Acta* 2006; 566: 55-59.
[10] Zhang X, Peng X, Jin W. Scanning electrochemical microscopy with enzyme immunoassay of the cancer-related antigen CA15-3. *Anal Chim Acta* 2006; 558: 110-114.
[11] Bard A J, Fan F R F, Kwak J. Scanning electrochemical microscopy. Introduction and principles. *Anal Chem* 1989; 61: 132-138.
[12] El-Said W A, Yea C H, Kim H et al. Cell-based chip for the Detection of Anticancer effect on HeLa Cells Using Cyclic Voltammetry. *Biosens Bioelectron* 2008 in press.
[13] Abe K, Niwa H, Iwase K et al. Endoderm-specific gene expression in embryonic stem cells differentiated to embryoid bodies. *Exp Cell Res* 1996; 229: 27-34.
[14] Wolf P, Rothermel A, Beck-Sickinger A G et al. Microelectrode chip based real time monitoring of vital MCF-7 mamma carcinoma cells by impedance spectroscopy. *Biosens Bioelectron* 2008; 24: 253-259.
[15] Kim B S, Choi J W Polyelectrolyte multilayer microcapsules : Self assembly and toward biomedical applications. *Biotechnol Bioprocess Eng* 2007; 12: 323-332.
[16] Yea C H Min J, Choi J W The fabrication of cell chips for use as bio-sensors. *Biochip J* 2007; 1: 219-227.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for determining a stem cell differentiation, comprising the steps of:
   (a) preparing the sensor for detecting the embryonic stem cell differentiation, said sensor comprising (i) an electrode which comprises a gold electrode as the working electrode, a platinum electrode as the counter electrode, and a Ag/AgCl electrode as the reference electrode; and (ii) 1-naphthyl phosphate (1-NP), a substrate for an alkaline phosphatase;
   (b) contacting the embryonic stem cells of interest to the sensor; and
   (c) measuring the phosphorylation or dephosphorylation of 1-NP for alkaline phosphatase on the cell through an electrical current signal which peaks at about 0.1 V, wherein the peak changes to negative voltage as the concentration of 1-NP decreases; and wherein if the embryonic stem cell comprises an alkaline phosphatase, the embryonic stem cell is an undifferentiated stem cell; and if the embryonic stem cell comprises no alkaline phosphatase, the embryonic stem cell is a differentiated stem cell.

* * * * *